United States Patent
Leung et al.

(10) Patent No.: US 6,204,432 B1
(45) Date of Patent: Mar. 20, 2001

(54) PA28 MODIFIED TRANSGENIC MICE

(75) Inventors: Wai-Ping Leung; Young Yang, both of San Diego, CA (US); Tobias Preckel, Walbronn (DE); Per Peterson, Bedminister, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/386,746

(22) Filed: Aug. 31, 1999

(51) Int. Cl.$^7$ .................. A01K 67/027; C12N 15/00; C12N 15/09; C12N 15/63

(52) U.S. Cl. .................. 800/18; 800/25; 435/320; 435/325; 435/463; 536/23.1; 536/23.5

(58) Field of Search .................. 800/18, 85; 536/23.1, 536/23.5; 435/320.1, 325, 463; 530/350

(56) References Cited

PUBLICATIONS

Preckel et al, 1999, Science, 286: 2162–2195.*

Ahn, Joon Young; Tanahashi, Nobuyuki; Akiyama, Kin–ya; Hisamatsu, Hiroshi; Noda, Chiseko; Tanaka, Keiji; Chung, Chin Ha; Shibmara, Naoki; Willy, Patricia J.; Mott, Joni D.; Slaughter, Clive A.; DeMartino, George N. Primary structures of two homologous subunits of PA28, a Y–interferon–inducible protein activator of the 20S proteasome. FEBS Letters 366, 37–42 (1995).

Ahn, Kwangseog; Erlander, Mark; Leturcq, Didier; Peterson, Per A.; Fruh, Klaus; Yang, Young. In Vivo Characterization of the Proteasome Regulator PA28. The Journal of Biological Chemistry, vol. 271, No. 30, pp. 18237–18242, Issue of Jul. 26, 1996.

Bluthmann, Horst; Kisielow, Pawel; Uematsu, Yasushi; Malissen, Marie; Krimpenfort, Paul; Berns, Anton; von Boehmer, Harald; Steinmetz, Michael. T–cell–specific deletion of T–cell receptor transgenes allows functional rearrangement of endogenous a– and B–genes. Nature, vol. 334, Jul. 14, 1988.

Chu–Ping, Ma; Slaughter, Clive A.; DeMartino, George N. Identification, Purification, and Characterization of a Protein Activator (PA28) of the 20 S Proteasome (Macropain). The Journal of Biological Chemistry, vol. 267, No. 15 Issue, pp. 10515–10523, May 25, 1992.

Chu–Ping, Ma; Willy, Patricia J.; Slaughter, Clive A.; DeMartino, George N. PA28, an Activator of the 20 S Proteasome, Is Inactivated by Proteolytic Modification at Its Carboxyl Terminus. The Journal of Biological Chemistry, vol. 268, No. 30 Issue, pp. 22514–22519, Oct. 25, 1993.

Conconi, Mariangela; Djavadi–Ohaniance, Lisa; Uerkvitz Wolfgang; Hendil, Klavs B.; Friguet, Bertrand. Conformational Changes in the 20S Proteasome upon Macromolecular Ligand Binding Analyzed with Monoclonal Antibodies. Archives of Biochemistry and Biophysics, vol. 362, No. 2, pp. 325–328, Feb. 15, 1999.

Coux, Olivier; Tanaka, Keiji; Goldberg, Alfred L. Structure and Functions Of The 20 S And 26 S Proteasomes. Annu. Rev. Biochem., 65:801–47, 1996.

Dick, Tobias P.; Ruppert, Thomas; Groettrup, Marcus; Kloetzel, Peter M.; Kuehn, Lothar; Koszinowski, Ulrich H.; Stevanovic, Stefan; Schild, Hansjorg; Rammensee, Hans–Georg. Coordinated Dual Cleavages Induced by the Proteasome Regulator PA28 Lead to Dominant MHC Ligands. Cell, vol. 86, 253–262, Jul. 26, 1996.

Driscoll, James; Brown, Michael G.; Finley, Daniel; Monaco, John J. MHC–Linked LMP gene products specifically alter peptidase activities of the proteasome. Letters To Nature, vol. 365, Sep. 16, 1993.

Dubiel, W.; Pratt, G.; Ferrell, K.; Rechsteiner, M. Purification of an 11 S regulator of the multicatalytic protease. J. Biol. Chem., vol. 267, Issue 31, 22369–22377, Nov. 1992.

Dubiel, Wolfgang; Pratt, Greg; Ferrell, Katherine; Rechsteiner, Martin. Purification of an 11 S Regulator of the Multicatalytic Protease. The Journal of Biological Chemistry, vol. 267, No. 31, pp. 22369–22377, Issue of Nov. 5, 1992.

Fehling, H.J.; Swat, W.; Laplace, C.; Kuhn, R.; Rajewsky, K.; Muller, U.; von Boehmer, H. MHC Class I Expression in Mice Lacking the Proteasome Subunit LMP–7. Science, vol. 265, 26/08, 94.

Flad, Thomas; Spengler, Bernhard, Kalbacher, Hubert, Brossart, Peter; Baier, Daniel; Kaufmann, Raimund; Bold, Peter; Metzger, Sabine; Bluggel, Martin; Meyer, Helmut E.; Kurz, Bernd; Muller, Claudia A. Direct Identification of Major Histocompatibility Complex Class I–bound Tumor–associated Peptide Antigens of a Renal Carcinoma Cell Line by a Novel Mass Spectrometric Method. Cancer Research 58, 5803–5811, Dec. 15, 1998.

Fruh, K.; Gossen, M.; Wang, K.; Bujard, H.; Peterson, PA; Yang, Y. Displacement of housekeeping proteasome subunits by MHC–encoded LMPs: a newly discovered mechanism for modulating the multicatalytic proteinase complex. The EMBO Journal, vol. 13, pp. 3236–3244, 1994.

Fruh, Klaus; Yang, Young. Antigen presentation by MHC class I and its regulation by interferon Y. The R.W. Johnson Pharmaceutical Research Institute, La Jolla, CA, 1999.

Gaczynska, Maria; Rock, Kenneth L.; Goldberg, Alfred L. Y–Interferon and expression of MHC genes regulate peptide hydrolysis by proteasomes. Letters to Nature, vol. 365, Sep. 16, 1993.

(List continued on next page.)

Primary Examiner—Scott D. Priebe
Assistant Examiner—Peter Paras, Jr.
(74) Attorney, Agent, or Firm—John W. Wallen, III

(57) ABSTRACT

A transgenic mouse with alterations in a PA28β gene is prepared by introduction of an altered PA28β gene into a host mouse. The resulting transgenic animals do not produce functional PA28 molecules. Cells and cell lines derived from these animals also contain the altered PA28β gene.

7 Claims, 4 Drawing Sheets

OTHER PUBLICATIONS

Gaczynska, Maria; Goldberg, Alfred L.; Tanaka, Keiji; Hendil, Klavs B.; Rock, Kenneth L. Proteasome Subunits X and Y Alter Peptidase Activities in Opposite Ways to the Interferon–y–induced Subunits LMP2 and LMP7. The Journal of Biological Chemistry, vol. 271, No. 29, pp. 17275–17280, Issue of Jul. 19, 1996.

Gaczynska, Maria; Rock, Kenneth L.; Spies, Thomas; Goldberg, Alfred L. Peptidase activities of proteasomes are differentially regulated by the major histocompatibility complex–encoded genes for LMP2 and LMP7. Proc. Natl. Acad. Sci. USA, vol. 91, pp. 9213–9217, Sep. 1994.

Gray, Carla W.; Slaughter, Clive A.; DeMartino, George N. PA28 Activator Protein Forms Regulatory Caps on Proteasome Stacked Rings. J. Mol. Biol. 236, 7–15 1994.

Groettrup, Marcus; Soza, Andrea; Eggers, Maren; Kuehn, Lothar; Dick, Tobias P.; Schild; Hansjorg Rammensee; Koszinowski, Ulrich H.; Kloetzel, Peter–M. A role for the proteasome regulator PA28a in antigen presentation. Letters to Nature, vol. 381, May 9, 1996.

Hendil, Klavs B.; Khan, Selina; Tanaka, Keiji. Simultaneous binding of PA28 and PA700 activators to 20 S proteasomes. Biochem. J. 332, 749–754, 1998.

Jackson, Michael.; Song, Elizabeth S.; Yang, Young; Peterson, Per A. Empty and peptide–containing conformers of class I major histocompatibility complex molecules expressed in *Drosophila melanogaster* cells. Proc. Natl. Acad. Sci. USA, vol. 89, pp. 12117–12121, Dec. 1992.

Jameson, SC; Carbone, FR; Bevan, MJ. Clone–specific T cell receptor antagonists of major histocompatibility complex class I–restricted cytotoxic T cells. JEM Abstracts: Jameson et al. 177 (6) : 1541.

Johnston, Steven C.; Whitby, Frank G.; Realini, Claudio; Rechsteiner, Martin; Hill, Christopher P. The proteasome 11S regulator subunit REGa (PA28a) is a heptamer. Protein Science, 6:2469–2473, 1997.

Knowlton, Randolph J.; Johnston, Steven C.; Whitby, Frank G.; Realini, Claudio; Zhang, Zhiguo; Rechsteiner, Martin; Hill, Christopher P. Structure of the proteasome activator REGa (PA28a). Letters to Nature, vol. 390, Dec. 11, 1997.

Li, Yuanhao; Chambers, James; Pang, Jesse; Ngo, Karen; Peterson, Per A.; Leung, Wai–Ping; Yang, Young. Characterization of the mouse proteasome regulator PA28b gene. Immunogenetics, 49:149:157, 1999.

Ma, CP; Willy, PJ; Slaughter, CA; DeMartino, GN. PA28, an activator of the 20 S proteasome, is inactivated by proteolytic modification at its carboxyl terminus. J. Biol. Chem., vol. 268, Issue 30, 22514–22519, Oct., 1993.

Ma, CP; Slaughter, CA; DeMartino, GN. Identification, purification, and characterization of a protein activator (PA28) of the 20 S proteasome (macropain). J. Biol. Chem., vol. 267, Issue 15, 10515–10523, May 1992.

Moore, Mark. W.; Carbone, Francis R.; Bevan, Michael J. Introduction of Soluble Protein into the Class I Pathway of Antigen Processing and Presentation. Cell, vol. 54, 777–785, 09, 1998.

Palmer, Amparo; Rivett, A. Jennifer; Thomson, Stuart; Hendil, Klavs B.; Butcher, Geoffrey W.; Fuertes, Graciela; Knecht, Erwin. Subpopulations of proteasomes in rat liver nuclei, microsomes and cytosol. Biochem. J. 316, 401–407, 1996.

Porgador, Angel; Yewdell, Jonathan W.; Deng, Yuping; Bennink, Jack R.; Germain, Ronald N. Localization, Quantitation, and In Situ Detection of Specific Peptide–MHC Class I Complexes Using a Monoclonal Antibody. Immunity, vol. 6. 715–726, Jun. 1997.

Realini, Claudio, Jensen, Christopher C.; Zhang, Zhi–guo; Johnston, Steven C.; Knowlton, J. Randolph; Hill, Christopher P.; Rechsteiner, Martin. Characterization of Recombinant REGa, REGB, and REGy Proteasome Activators. The Journal of Biological Chemistry, vol. 272, No. 41, pp. 25483–25492, Issue of Oct. 10, 1997.

Realini, Claudio; Rogers, Scott W.; Rechsteiner, Martin. Proposed roles in protein–protein association and presentation of peptides by MHC Class I receptors. FEBS Letters 348, 109–113, 1994.

Rivett, A. Jennifer. Intracellular distribution of proteasomes. University of Bristol, 1998.

Rock, Kenneth L.; Goldberg, Alfred L. Degradation of Cell Proteins and the Generation of MHC Class I–Presented Peptides. Annu. Rev. Immunol., 17:739–79, 1999.

Song, Xiaoling; von Kampen, Jan; Slaughter, Clive A.; DeMartino, George N. Relative Functions of the a and B Subunits of the Proteasome Activator, PA28. The Journal of Biological Chemistry, vol. 272, No. 44, pp. 27994–28000, Issue of Oct. 31, 1997.

Van Kaer, Luc; Ashton–Rickardt, Philip G.; Elchelberger, Maryna; Gaczynska, Maria; Nagashima, Kumiko; Rock, Kenneth L.; Goldberg, Alfred L.; Doherty, Peter C.; Tonegawa, Susumu. Altered Peptidase and Viral–Specific T Cell Response in LMP2 Mutant Mice. Immunity, vol. 1, 533–541, Oct., 1994.

Vinitsky, Alexander; Anton, Luis C.; Snyder, Heide Link; Orlowski, Marian; Bennick, Jack R.; Yewdell, Jonathan W. The Generation of MHC Class I–Associated Peptides Is Only Partially Inhibited by Proteasome Inhibitors. The American Association of Immunologists, 1997.

Vitiello, Antonella; Sette, Alessandro; Yuan, Lumil; Farness, Peggy; Southwood, Scott; Sidney, John; Chestnut, Robert W.; Grey, Howard M.; Livingston, Brian. Comparison of cytotoxic T lymphocyte responses induced by peptide or DNA immunization: implications on immunogenicity and immunodominance.

Yang, Young; Fruh, Klaus; Kwangseog, Ahn, Peterson, Per A. In Vivo Assembly of the Proteasomal Complexes, Implications for Antigen Processing. The Journal of Biological Chemistry, vol. 270, No. 46, pp. 27687–27694, Issue of Nov. 17, 1995.

Yang, Young; Sempe', Pascal; Peterson, Per A. Molecular Mechanisms of Class I Major Histocompatibility Complex Antigen Processing and Presentation. Immunologic Research, 15:208–233, 1996.

\* cited by examiner

US 6,204,432 B1

PA28 MODIFIED TRANSGENIC MICE

FIELD OF THE INVENTION

The present invention relates to transgenic non-human animals wherein a PA28β gene is altered, producing an animal lacking functional PA28 protein.

BACKGROUND OF THE INVENTION

The presentation of antigenic peptides by class I major histocompatibility complex (MHC) molecules plays a central role in the cellular immune response, since immune surveillance for detection of viral infections or malignant transformations is achieved by cytotoxic T lymphocytes (CTL), which inspect peptides bound to class I molecules on the surface of most cells (Yang et al., 1996). CTL eliminate infected cells by recognizing foreign antigens (Rock and Goldberg, 1999), which are processed in a proteasome-dependent manner and are presented by the MHC class I molecules. The multisubunit proteasomes, which degrade cytoplasmic proteins in an ATP and ubiquitin-dependent manner, are required for the generation of the antigenic peptides. Biochemical studies with proteasome inhibitors (Rock et al., 1994; Vinitsky et al., 1997) have provided evidence that the proteasome is responsible for the generation of class I-binding peptides. Indeed, in vitro enzymatic studies of isolated proteasomes have demonstrated that altered molecular organization of the proteasome induced by IFN is responsible for functional changes in the catalytic activity. This ultimately results in changes to antigen processing (Driscoll et al., 1993; Fruh and Yang, 1999; Gaczynska et al., 1996; Gaczynska et al., 1993; Gaczynska et al., 1994). Moreover, in vivo evidence obtained from analysis of LMP2 or LMP7 knock-out mice (Fehling et al., 1994; Van Kaer et al., 1994) indicates that IFN-induced proteasome subunits play a major role in proteasome-mediated antigen processing. Both LMP2 and LMP7 knock-out mice are deficient in the generation of a subset of antigenic peptides. Thus, the proteasome subunit exchange is a fundamental mechanism for modulating proteasome activities by cytokines during immune responses (Fruh et al., 1997).

In eukaryotes, proteasome activities are modulated by specific regulatory proteins that form complexes with proteasomes (Yang et al., 1996). Two regulatory complexes, the ATPase complex and PA28, have been studied to some extent. The ATPase complex associates with the 20 S proteasome in an ATP-dependent manner, resulting in the 26 S proteasome (Rock and Goldberg, 1999). This 26 S proteasome is involved in the degradation of protein substrates in an ubiquitin-dependent manner (Rock and Goldberg, 1999). The proteasome regulator PA28 has been shown to associate with the 20 S proteasome in vitro (Chu-Ping et al., 1992; Chu-Ping et al., 1993) and in vivo (Yang et al., 1995) in an ATP-independent manner. Association of these regulatory complexes appears to be reversible and regulated by phosphorylation (Yang et al., 1995). It is conceivable that evolutionary divergence of these regulatory complexes is coupled with their functional specialization and that regulatory mechanisms exist that render antigenic peptides more likely to become available to class I molecules during immune responses. Antigen degradation could occur in two steps, namely, initial degradation of whole antigen into intermediate sized fragments by 26 S proteasomal complexes followed by degradation of these fragments by the PA28/20 S proteasomal complexes to produce peptides of 8–10 residues in length (Fourie and Yang, 1998; Fruh and Yang, 1999). Indeed, in vitro kinetic studies on the influence of PA28 on peptide cleavage and specificity of the proteasome (Chu-Ping et al., 1992) indicate that PA28 changes the cleavage behavior of the proteasome in a characteristic qualitative and quantitative manner. In the absence of PA28, the proteasome digests substrates by consecutive and independent single cleavages. Upon association with PA28, products generated by two flanking cleavages appear immediately as main products, while the generation of single-cleavage products is strongly reduced (Dick et al., 1996). Since this PA28-induced, coordinated double-cleavage mechanism appears to optimize the generation of dominant T-cell epitopes (Groettrup et al., 1996), the regulation of PA28 expression by IFN plays an essential role in proteasome-mediated antigen processing (Ahn et al., 1996; Fruh and Yang, 1999).

The peptidase activities of the proteasome can be activated in vitro by the proteasome regulator PA28α, β, or both (Realini et al., 1997; Song et al., 1997). In mice, there are at least two functional copies for PA28α, while PA28β has only one functional copy (Li et al., 1998). PA28α itself is capable of forming homoheptamers in vitro (Johnston et al., 1997; Knowlton et al., 1997). An in vivo role for PA28 remains unknown, although PA28 has been implicated in playing a role in MHC class I antigen presentation (Dick et al., 1996; Groettrup et al., 1996). The underlying mechanism by which PA28 modulates proteasome function in antigen processing remains elusive. More specifically the individual roles for PA28α and PA28β in vivo on immuno-proteasomes and their relationship to each other have yet to be understood. Understanding the roles of these proteins, and specifically PA28β, should aid in understanding therapeutically important disease states including auto-immunity, transplantation, inflammation, and cancer immunology. Greater understanding of the roles that proteasome-dependent antigen presentation for these conditions is expected to open new mechanisms of therapeutic intervention or modulation.

The present invention provides a means to dissect the functional role of PA28 in different cell types, such as cytotoxic T cells and antigen presenting cells. The PA28β gene was disrupted by homologous recombination and PA28 deficient cells were prepared. The in vivo effect of deficient proteasome-dependent major histocompatibility complex (MHC) classes I antigen processing is analyzed in PA28-deficient transgenic animals.

SUMMARY OF THE INVENTION

To understand the functional role of PA28 in different cell types, mice that do not express the functional PA28 were generated by homologous recombination (HR) in embryonic stem (ES) cells and are disclosed herein. Cell lines that are derived from these mice are also disclosed herein. These mice, including the cell lines derived from them, provide a valuable animal model and tools to understand the function of PA28 and to evaluate the therapeutic effects of drugs that modulate the function or the expression of PA28 and PA28-mediated proteasome activity equivalents in human cells.

DETAILED DESCRIPTION OF THE INVENTION

Figure 1:
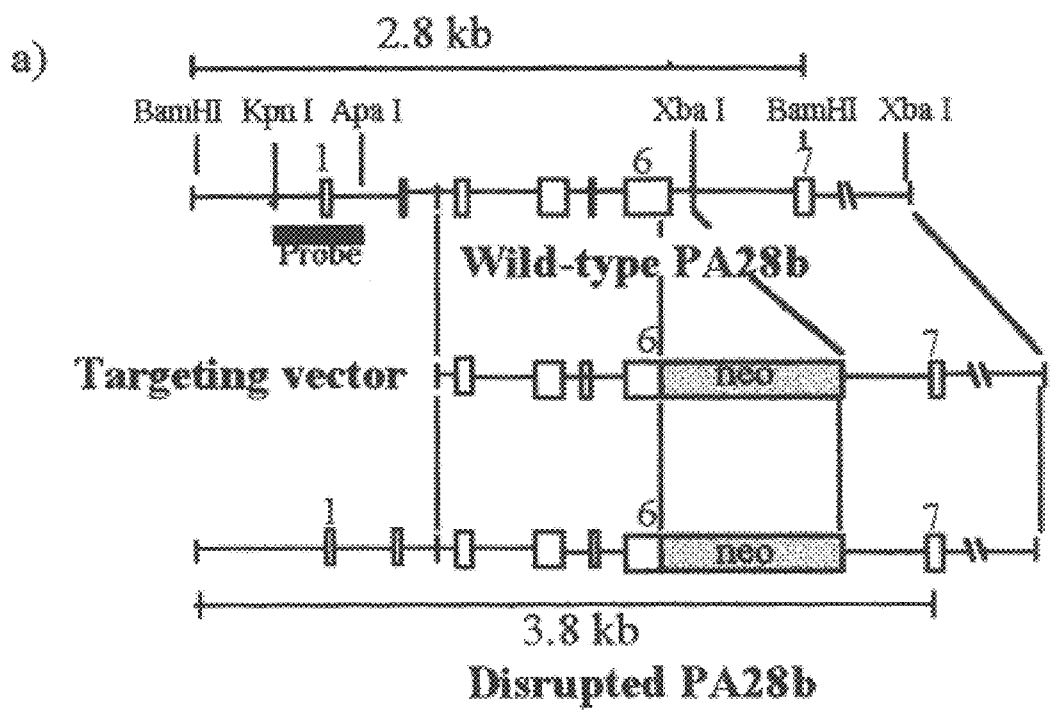
FIGS. 1(A–B). Generation of PA28β–/– mice. a, A schematic diagram showing the PA28β1 locus, targeting vector, and the resulting disrupted PA28β gene. b, Southern hybridization analysis of representative PA28β+/+ and PA28β+/– embryonic stem cells using genomic DNA digested with BamHI and the 0.65-kb KpnI-ApaI DNA fragment as a probe. The functional PA28β1 gene was detected as a 2.8 kb DNA band and the disrupted PA28β1* gene as a 3.8 kb band, while the PA28β2 pseudogene was contained within a 6.5 kb DNA band.
Figure 1:
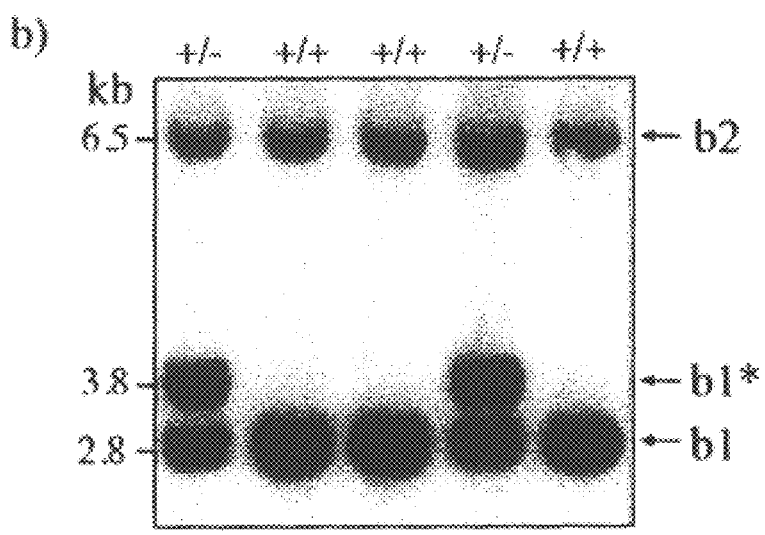

The PA28 knockout mice that were generated in the present invention provide a model in which the PA28β gene was disrupted by homologous recombination (HR). The process of generating the knockout mice can be divided into 4 basic stages:

1. cloning of PA28β gene and preparation of DNA construct for transfection of embryonic stem (ES) cells;
2. isolating ES cells in which the PA28β gene has been disrupted by HR;
3. generating chimeric mice from mouse embryos injected with the knockout ES cells; and
4. breeding chimeric mice to obtain knockout mice through germline
5 transmission.

The present invention utilizes a cloned genomic DNA encoding the PA28 protein and describes the cloning and characterization of the mouse PA28β gene. Transgenic animals are generated which have an altered PA28β gene. The alterations to the naturally occurring gene can be modifications, deletions and substitutions. Modifications and deletions render the naturally occurring gene nonfunctional, producing a "knockout" animal. Substitution of the naturally occurring gene for a gene from a second species results in an animal that produces the gene product of the second species. Substitution of the naturally occurring gene for a gene having a mutation results in an animal that produces the mutated gene product. These transgenic animals are critical for drug antagonist or agonist studies, the creation of animal models of human diseases, and for eventual treatment of disorders or diseases associated with PA28-mediated responses. A transgenic animal carrying a "knockout" of PA28 is useful for the establishment of a non-human model for diseases involving PA28 equivalents in the human.

A transgenic mouse carrying the disrupted PA28β gene was generated by homologous recombination of a target DNA construct with the endogenous gene in the chromosome. The DNA construct was prepared from a genomic clone of PA28 which was isolated from a genomic DNA library.

The term "animal" is used herein to include all vertebrate animals except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomal replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The altered PA28β gene generally should not fully encode the same PA28 as native to the host animal, and its expression product should be altered to a minor or great degree, or absent altogether. However, it is conceivable that a more modestly modified PA28β gene will fall within the scope of the present invention.

The genes used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro [M. J. Evans et al, Nature 292: 154–156 (1981); M. O. Bradley et al, Nature 309: 255–258 (1984); Gossler et al. Proc. Natl. Acad. Sci. USA 83: 9065–9069 (1986); Robertson et al., Nature 322, 445–448 (1986); S. A. Wood et al. Proc. Natl. Acad. Sci. USA 90: 4582–4584 (1993)]. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)).

Since PA28 is an independent component of a complex mechanism, the proteins, including that encoded by PA28β DNA, must be examined both individually and as a group if their contribution to the mechanisms are to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described in 1987 (Thomas et al., Cell 51:503–512, (1987)) and is reviewed elsewhere (Frohman et al., Cell 56:145–147 (1989); Capecchi, Trends in Genet. 5:70–76 (1989); Baribault et al., Mol. Biol. Med. 6:481–492, (1989); Wagner, EMBO J. 9: 3025–3032 (1990); Bradley et al., Bio/Technology 10: 534–539 (1992)).

Techniques are available to inactivate or alter any genetic region to any mutation desired by using targeted homologous recombination to insert specific changes into chromosomal genes. Homologous recombination was reported to be detected at frequencies between $10^{-6}$ and $10^{-3}$ (Lin et al, Proc. Natl. Acad. Sci. USA 82:1391–1395 (1985); Smithies et al., Nature 317: 230–234 (1985); Thomas et al., Cell 44:419–428, (1986); Song et al., Proc. Natl. Acad. Sci. USA 84:6820–6824 (1987)). Non-homologous plasmid-chromosome interactions are more frequent, occurring at levels $10^5$-fold (Lin et al, Proc. Natl. Acad. Sci. USA 82:1391–1395 (1985)) to $10^2$-fold (Thomas et al., Cell 44:419–428 (1986); Song et al., Proc. Natl. Acad. Sci. USA 84:6820–6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformed cells for homologous insertion, followed by screening individual clones (Kim et al, Nucleic Acids Res. 16:8887–8903 (1988); Kim et al., Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most powerful approaches developed for selecting homologous recombinants is the positive-negative selection (PNS) method developed for genes (such as PA28) for which no direct selection of the alteration exists (Mansour et al., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Non-homologous recombinants are selected against by using the Herpes Simplex virus thymidine kinase (HSV-TK) gene flanking the DNA construct. Cells with non-homologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). By this counter-selection, the number of homologous recombinants in the surviving transformants can be increased.

As used herein, a "targeted gene" or "knockout" is a DNA sequence introduced into the germ line of a non-human animal by way of human intervention, including but not limited to, the methods described herein. The targeted genes of the invention include DNA sequences that are designed to specifically alter cognate endogenous genes.

All the above applications have to be verified in animal tests and eventually clinical trials. One approach to determine the functional role of the drug target is to study the defects resulting from the disrupted gene in a whole animal. The PA28 knockout mice that have been generated and are disclosed herein will allow the definition of the function of PA28 that is critical in deciding the types of modulators are most suitable in therapies.

Any PA28 function that is detected in the knockout mice of the present invention would provide evidence of the existence of alternative novel PA28 subtypes which may then be isolated from the knockout mice of the present invention.

The absence of functional PA28 in the knockout mice of the present invention are confirmed, for example, in RNA analysis, protein expression detection, MHC-I peptide expression assays, CTL lytic assays, and other PA28 functional studies. For RNA analysis, RNA samples are prepared from different organs of the knockout mice and the PA28 transcripts are detected in Northern blots using oligonucleotide probes specific for the transcript.

Polyclonal antibodies that are specific for the mouse PA28 are produced. The absence of intact PA28 in the knockout mice are studied, for example, in Western Blot analysis of various cell types, protein samples are prepared from different organs of the knockout mice, and in immunoprecipitation analysis of various cell types using PA28-specific or proteasome-specific antibodies. Alternatively, functional assays are performed using preparations of different cell types collected from the knockout mice.

Interferon-inducible PA28α and β (Ahn et al., 1995; Ahn et al., 1996; Realini et al., 1994) have been identified as proteasome activators in vitro (Chu-Ping et al., 1992; Dubiel et al., 1992). The role to which PA28 plays in vivo, however, has remained unclear.

The present invention demonstrates that mice with a disrupted PA28β gene have substantially altered the spectrum of peptides presented by MHC class I molecules.

Generation of MHC class I epitopes from exogenous or endogenous antigens is severely impaired, resulting in reduced CTL responses in PA28β-/- mice. The present invention demonstrates the surprising observation that PA28β-/- mice not only lack PA28β but also PA28α polypeptide. Thus the formation of the PA28 hetero-oligomer is obligatory in vivo and PA28β-/- mice are functionally equivalent to PA28α-/-/β-/- mice. Further, PA28 is shown to function as a chaperone to promote the incorporation of the interferon inducible catalytic subunits LMP2/7 and MECL1 (Fruh and Yang, 1999; Rock and Goldberg, 1999) into the immuno-proteasome. Thus, by inducing the assembly of the immuno-proteasome PA28 modulates in vivo proteasome-dependent class I antigen processing.

The following Examples are presented for the purpose of illustrating the present invention and are not to be construed as a limitation on the scope of this invention.

EXAMPLE 1

Gene Targeting

In this knockout construct, the mouse PA28β gene was disrupted by deleting a portion of exon 6 and the 3' intron from exon 6. A neomycin resistance gene was used to replace the deleted region.

The knockout construct was composed of parts arranged in a 5' to 3' order, as illustrated in FIG. 1: (1) A 0.85-kb DNA fragment from a 129/Ola mouse genomic clone covering exons 3–6 of the PA28 gene, (2) A 1.2 kb DNA cassette containing a neomycin resistant gene with its own promoter and polyadenylation signal, (3) A 6-kb XbaI-XbaI DNA fragment covering exons 7– 11 of the PA28β gene. The PA28β gene and the neomycin resistant gene were in the same orientation of transcription.

Transfection of ES Cells With the PA28 DNA Construct

Embryonic stem (ES) cells E14 (Hooper et al., 1987, HPRT-deficient (Lesch-Nyhan) mouse embryos derived from germ line colonization by cultured cells. Nature 326, 292–295) were maintained at an undifferentiated stage by co-culturing with embryonic fibroblasts (EF) and in culture medium DMEM (15% FCS, 1 mM sodium pyruvate, 0.1 mM b-mercaptoethanol, 2 mM L-glutamine, 100 U penicillin and 100 U streptomycin) containing 1000 U/ml leukemia inhibitory factor (LIF) (Gibco). EF cells were primary fibroblast cultures prepared from day 15–17 mouse fetuses according to the method described by Robertson (Robertson, E. J. (1987) Embryo-derived Stem Cell Lines. In: Teratocarcinomas and Embryonic Stem Cells. E. J. Robertson, ed. (Oxford, Washington DC: IRL Press), p 71–112.). EF were treated with 10 mg/ml mitomycin C (Sigma) in culture medium for 2 hours to stop cell division prior to the use as feeder cells.

For DNA transfection, the DNA construct was linearized by NotI digestion. DNA was then precipitated by 2 volumes of ice cold ethanol at −20° C. for 1 hour. Precipitated DNA was pelletted by centrifugation, rinsed once with 0.5 ml 70% ethanol, air dried and then dissolved at 1 mg/ml in phosphate-buffered saline (Gibco). ES cells were harvested by trypsin treatment and resuspended at $6.25 \times 10^6$ cell/ml in culture medium. DNA construct (20 μg) was added to 0.8 ml of ES cell suspension for electroporation at 250 μF and 340 Volts using the Gene Pulser (BioRad).

Transfected ES cells were plated onto EF coated 90 mm plates at $2.5 \times 10^6$/plate in culture medium. Two days later, cells were subjected to drug selection in medium containing 400 μg/ml G418 (Geneticin, Gibco) and 2 μM GANC (Cytosin, Syntex). Culture medium was changed daily. Massive cell death was obvious starting day 4 and most of the dead cells were removed through daily medium change. Surviving cell colonies were observable under microscope by day 7 and by day 10 they were visible on the plates without a microscope.

PCR Screen of Transfected ES Cells for Homologous Recombination

The size of ES colonies on day 11 after transfection was large enough for PCR screening. To collect cell colonies, culture medium in the 90 mm plates was aspirated and 10 ml PBS was added. Individual cell colonies were located with the aid of a stereomicroscope, collected in a 20 ml volume and transferred into 96 well-plates. To prepare single cell suspension of the ES colonies, 25 μl of 0.25% trypsin (Gibco) was added per well in 96 well-plates. After 8 minutes of trypsin treatment at 37° C., 25 μl of culture medium was added. All the ES colonies were still maintained in culture as master plates while screening by PCR for homologous recombination events was performed. To prepare master plates, 60 μl of each cell sample was transferred to 96-well plates which had been coated with EF cells and contained 180 μl/well of the culture medium containing G418 and GANC.

For the first round PCR screen, each cell lysate sample was prepared from 12 cell colonies which arrayed as one row of samples in the 96 well-plates. After the preparation of master plates, the remaining cell samples of about 90 μl/well on every row of the plates were pooled. Cells were pelleted in tubes by centrifugation for 1 minute. After draining all the medium, cells were lysed by adding 30 μl distilled water and brief vortexing. Cell lysates were prepared by first heating at 95° C. for 10 minutes, cooling to room temperature and followed by an addition of 1 μl proteinase K (10 mg/ml in water) with brief vortexing, a 90 minute incubation at 50° C. for proteinase K digestion, and then 10 minutes at 95° C. for heat inactivation of proteinase K.

PCR was carried out using the 9600 GeneAmp system (Perkin Elmer). The reaction mixtures contained 5 μl cell lysate, 4 μM of each of the two oligonucleotide primers, 200 μM each of dATP, dTTP, dCTP, and dGTP, and 5 U Ampli-Taq DNA polymerase in PCR buffer (10 mM Tris-Cl, pH8.3, 50 mM KCl, 1.5 mM $MgCL_2$ and 0.001% w/v gelatin). The reaction condition was 3 cycles of 2 minutes at 94° C., 2 minutes at 60° C., and 2 minutes at 72° C., then 40 cycles of 15 seconds at 94° C., 15 seconds at 60° C., and 1 minutes at 72° C., followed by 7 minutes at 72° C.

ES cells with the targeted gene were detected by polymerase chain reaction using neomycin resistant gene-specific oligonucleotide (5'-CAAAACCACACTGCTCGACATTG-3') [SEQ.ID.NO.: 1] and PA28 intron 2-specific specific oligonucleotide (5'-GAGTAACCCACCAGTTCACCTTAA-3') [SEQ.ID.NO.: 2] and the size of the amplified DNA is expected to be about 1.2 kb. To detect the specific DNA fragment amplified by PCR, 20 μl of the PCR samples were separated according to size by 1% agarose gel electrophoresis, blotted onto Hybond-N+ nylon membranes (Amersham), and hybridized to the $P^{32}$-labelled PA28β gene-specific oligonucleotide probe (5'-TCCGAACCTTCATGCTTACTCAAG-3') [SEQ.ID.NO.: 3]. The PCR samples that contained a 1.2-kb DNA fragment that was detected by the oligonucleotide probe were considered as putative positive groups for further screening.

ES cells in master plates after 3–4 days culture were ready for splitting. Cell colonies in the positive groups were screened individually by a second round of PCR to identify the positive individual colonies. To maintain the positive groups in culture, cells in the wells were trypsinized by first removing the culture medium, rinsing once with 50 µl PBS, treating with 40 µl 0.25% trypsin for 5 minutes at 37° C., followed by adding 90 µl culture medium. Cells were then resuspended and 20 µl of the cell samples were transferred to master plates which had been coated with EF and filled with 200 µl culture medium containing G418 and GANC. The remaining cells (110 µl/well) were transferred into eppendorf tubes. Cell lysates were prepared and homologous recombination signals were amplified by PCR and detected by hybridization as described in the previous paragraphs.

Confirmation of Homologous Recombination by Genomic Southern Hybridization

Homologous recombination was confirmed by Southern hybridization. ES cells derived from the positive colonies in PCR screen were expanded in culture and DNA was extracted as described by Maniatis et al. (Maniatis, T.; Fritsch, E. F.; Sambrook, J. (1982) Molecular Cloning, Cold Spring Harbor Laboratory pp. 280–281). Genomic DNA samples of the putative knockout cell lines were digested with the restriction enzymes BamHI, separated by 1% agarose gel electrophoresis, blotted onto Hybond-N+ nylon membranes (Amersham) and hybridized with a 0.65-Kb DNA fragment specific for the mouse PA28β gene. This probe is the 0.65-Kb KpnI—ApaI DNA fragment as shown in FIG. 1a. As shown in figure 1b the functional PA28β1 gene was detected as a 2.8-kb DNA band and the disrupted PA28β1* gene as a 3.8-kb band, while the PA28β2 pseudogene was contained within a 6.5-kb DNA band.

Generation of Chimeric Mice by Embryo Injection

Mouse embryos at 3.5 day gestation stage were collected from the uteri of super-ovulated C57BL/6J mice. About 10–15 ES cells were injected into the blastocoel cavity of the embryos. Injected embryos were transferred into the uteri of pseudo-pregnant CD1 mice at 2.5 day gestation. Mice developed from these embryos were born 17 days later. Since the ES cells used were derived from the 129 Ola mouse strain with the dominant agouti coat color genes, chimeric mice were identified by the agouti coat color from ES derived cells, versus the black color from C57BL/6J mouse embryos.

ES Germline Mice Obtained by Chimeric Mouse Breeding

Chimeric mice were bred with C57BL/6J mice. These crosses are performed to test for the germline transmission of ES cells. Some of the progeny from the breeding are expected to be agouti if the chimeric male had germ line cells derived from ES cells which carry the dominant agouti coat color genes. The disrupted PA28β gene in mice was detected by genomic hybridization as described in the previous section. Genomic DNA is purified from about 1 cm of tail from each agouti mouse after weaning. The genomic DNA is isolated as described (Laird et al., supra), followed by phenol and phenol:chloroform extractions and ethanol precipitation. Genomic DNAs are digested with BamHI, and hybridized with the 0.65 kD Kpn-ApaI DNA fragment specific for the PA28β gene as described earlier.

Generation of Homozygous Knockout Mice from Breeding of Hetrozygous Knockout Mice Female heterozygous knockout mice were mated with C57BL/6J mice or wild-type male littermates. It is expected that half of the male pups carry only the disrupted gene and half of the female pups are heterozygous for the disrupted gene. Surviving offspring were genotyped by RT-PCR as described above. Homozygous female mice were obtained by further breeding of heterozygous females with knockout males. Homozygous PA28β−/− mice, which were healthy and fertile, were born at the expected Mendelian frequency and exhibited normal growth, implying that PA28β is not essential for proteasome-mediated cellular functions.

EXAMPLE 2

Characterization of PA28 Knockout Mice and Cells Derived From the Mice

PA28β−/− mice contained numbers of macrophages, T and B cells that were equivalent to wild-type mice. Also, PA28−/− splenic T and B cells expressed wild-type levels of CD4, CD8, CD3-e, TCR-ab, CD23, CD25, CD28, CD45, CD69, and MHC class II molecules as determined by fluorescence activated cell sorting (FACS). Surprisingly, FACS analysis demonstrated that PA28β−/− mice expressed wild-type level of MHC class I molecules.

We examined the quality of peptides bound to class I molecules using the class I thermostability assay (Jackson et al., 1992). Class I molecules expressed in PA28β−/− cells were less stable than in wild-type cells, indicating the acquisition of inferior peptides, which do not stabilize class I heterodimers to the same extent as in the wild-type cells. A clear difference in the spectrum of peptides presented by class I molecules between wild-type and PA28β−/− cells was observed, revealing a 70% reduction in the production of hydrophobic peptides (eluants at 30–35% of acetonitrile) in PA28β−/− cells as shown in the chromatograph in FIG. 2a. This difference in class I-presented peptides remained after induction of the cells with interferon (Realini et al., 1997), suggesting that the deficiency of PA28β cannot be compensated for by up-regulating other MHC components involved in antigen presentation.

Figure 2:
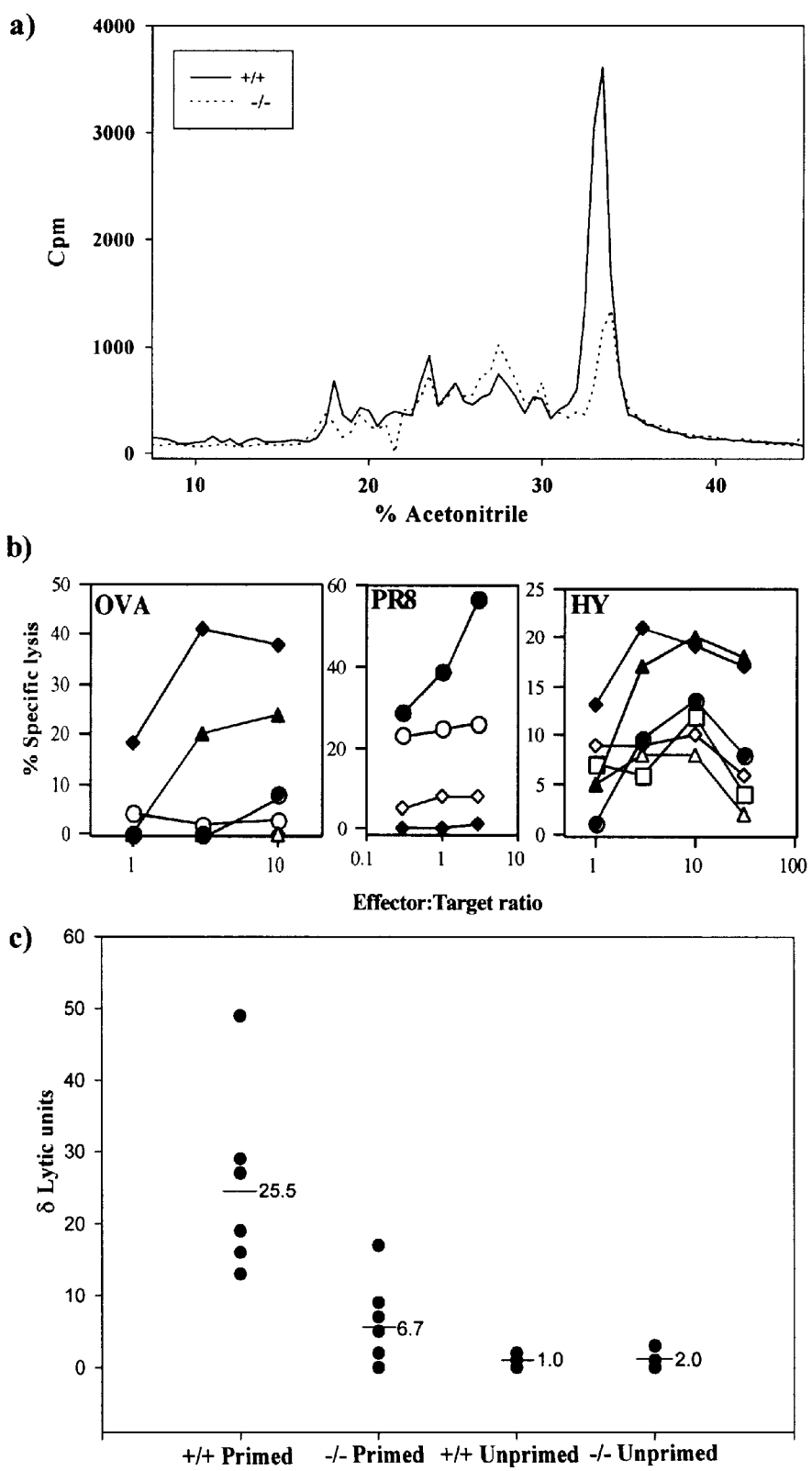
FIG. 2. Processing of exogenous and endogenous antigens. a, HPLC profiles of peptides elute from immunoprecipitated class I kb molecules of tritiated PA28β–/– and wildtype cells (+/+) with a monoclonal antibody Y3 as described (Flad et al., 1998). b, Left panel. Presentation of Ova8 was determined after the introduction of ovalbumin at 0 (circles), 3 (triangles), or 30 (diamonds) mg/ml into LPS blasts of wildtype (filled symbols) and PA28β–/– (open symbols) mice by hypertonic loading (Moore et al., 1988). After osmotic lysis of pinocytic vesicles the cells were cultured for 30 min at 37° C., chromium labeled for 1 h at 37° C. and assayed for their susceptibility to lysis by the Ova8 specific CTL clone B3 (Jameson et al., 1993). Middle panel. Presentation of NP366 was determined using peritoneal macrophages of wildtype and PA28β–/– mice infected with influenza virus PR8 at 1 PFU/cell during 1 h labeling with chromium. Susceptibility of macrophages to lysis by an NP366-specific CTL clone (Vitiello et al., 1997) at the indicated effector:target ratios was assayed in a chromium release assay. Right panel. Presentation of the male self-antigen HY was determined using HY specific CTLs (Bluthmann et al., 1988) as effectors in a chromium release assay. LPS blasts from two male wildtype mice (filled diamonds and filled triangles) or three male PA28β–/– mice (open symbols) were used as targets. LPS blasts from a female wildtype mouse (filled circle) served as a negative control. c, Ova8-specific CTL responses were assayed using mice primed and boosted with 100 μg alum-precipitated ovalbumin intraperitoneally as described (Jacoby et al., 1984). Splenocytes were restimulated in vitro with 1 μM Ova8 and IL-2 and used as effectors in a chromium release assay. Ova8 loaded EL4 cells were used as targets. CTL responses of non-primed mice were analysed in the same fashion. Net lytic units (LU20) are indicated.

To study the influence of PA28 on the generation of CTL epitopes, we monitored the generation of two epitopes (Ova8 and NP366) derived from the antigens ovalbumin and influenza nuclear protein, respectively. Ovalbumin was introduced into the cytoplasm of LPS blasts from wild-type and PA28β−/− mice and the presentation of the class I Kb-restricted Ova8 CTL epitope was assayed. FACS staining of the ovalbumin-loaded LPS blasts with a monoclonal antibody recognizing the class I Kb-β2m-Ova8 trimer (25D1.16 (Porgador et al., 1997)) demonstrated that the Ova8 epitope was presented in wildtype but not in the PA28β−/− cells. Importantly, CTL assays demonstrated that the Ova8-specific T cell clone B3 (Jameson et al., 1993) vigorously lysed the ovalbumin-loaded LPS blasts from wild-type but not PA28β−/− mice as seen in FIG. 2b, left panel. The extent of the B3-specific killing was dependent on the amount of ovalbumin delivered into the target cells. No difference was observed upon addition of synthetic Ova8 peptide, eliminating the possibility that PA28β−/− cells are inefficient CTL targets. In addition, the observation that the difference in the presentation of antigens or in in vivo CTL responses diminished when target cells were treated with the proteasome inhibitor lactacystin, further suggests that PA28 exerts its influence on MHC antigen processing via a proteasome-mediated pathway.

The processing of endogenous antigens was investigated by comparing the ability of LPS blasts from wild-type and PA28−/− mice to process and present the male self-antigen HY. CD8-enriched splenocytes from female mice bearing a transgenic T cell receptor specific for the $D^b$-restricted HY antigen (FIG. 2b, right panel) were used as responders. HY-specific CTL lysed male wild-type LPS blasts. However, they failed to kill male PA28β−/− and female wild-type cells, demonstrating that the endogenous HY self-antigen is not processed in PA28β−/− cells. Importantly, influenza virus infected PA28β−/− cells were significantly less sensitive to lysis by NP366-specific CTL as seen in FIG. 2b, middle panel. Thus, the absence of PA28β affects the processing of exogenous and endogenous antigens.

To determnine the role of these antigen processing defects for the generation of an immune response, wild-type and PA28β−/− mice were immunized with ovalbumin and assayed for the Ova8-specific CTL response as shown in FIG. 2c (specific killing expressed as net lytic units). While CTL from ovalbumin primed wild-type mice lysed peptide-treated target cells, the CTL response in PA28β−/− mice was significantly lower than in wild-type littermates. By contrary, no difference in CTL responses was observed when PA28β−/− mice and wild-type littermates were primed with Ova8 peptide. These data strongly suggest that the antigen processing defects in PA28β−/− cells resulted in impaired in vivo priming of CTL.

Figure 3:
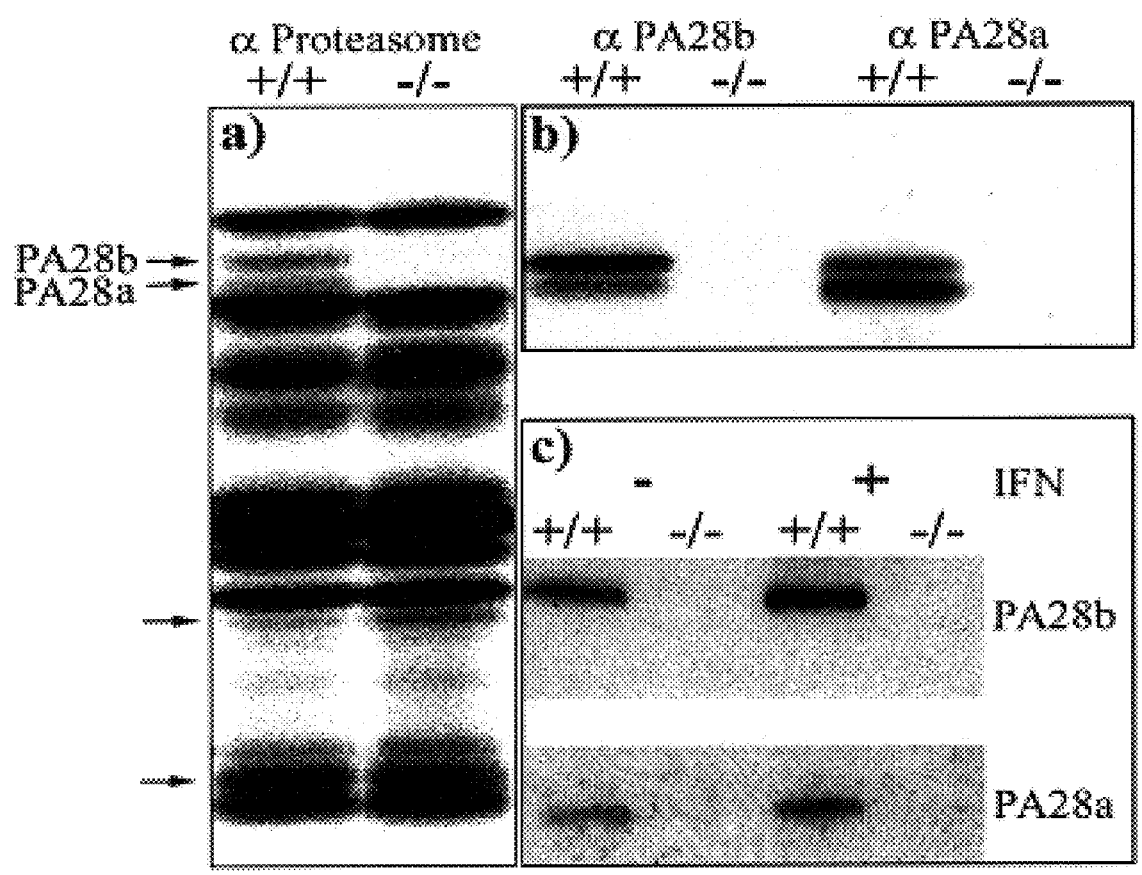
FIGS. 3(A–C). Expression of PA28α and β in PA28β–/– and wildtype mice. a, Co-immunoprecipitation of PA28 and proteasome. Cells were metabolically labeled for 2 h followed by a 4-h chase in the presence of the proteasome inhibitor lactacystin and lysed with buffer containing 1% digitonin. Immunoprecipitations were performed using a C9-specific antiserum. Catalytic subunits Y and LMP7 are indicated with arrows. It was found that lactacystin treatment not only stabilizes the association of proteasome and PA28 but also results in an increased electrophoretic mobility of LMP7. b, Immunoprecipitation analysis of PA28α and β expression. Splenocytes were metabolically labeled for 30 min. Immunoprecipitations were carried out with PA28β- or α-specific antisera. c, Immunoblotting analysis of PA28α and β expression. Splenocytes were lysed in SDS sample buffer, the samples were separated electrophoretically, immunoblotted, and probed with PA28α- or β-specific antisera.

How does a deficiency in PA28β lead to a defect in MHC antigen presentation? Without wishing to be bound by theory, one possibility is that in vivo PA28α or β regulate the proteasome independent of each other; thus when PA28β is lacking, proteasome function is skewed. Alternatively, PA28α and β could be dependent on each other, as is suggested by the observation that they are co-regulated and have identical half-lives (Ahn et al., 1996). To test these theories, we examined the production of PA28α mRNA and protein. First we determined that the expression level of PA28 α MRNA in PA28β−/− mice was equivalent to wild-type mice. To determine whether the alteration of antigen processing in PA28β−/− mice is attributed to PA28α, we examined whether in the absence of PA28β the subcellular localization and half-life of PA28α is altered. Immunofluoresence microscopy showed that while PA28α and b were expressed mainly in the cytoplasm of wildtype cells, no expression of PA28α and β was detected in PA28β−/− cells. Co-immunoprecipitation experiments showed that under conditions where PA28 remains associated with the proteasome in wild-type cells, no proteasome-associated PA28 polypeptides were detected in PA28β−/− cells, shown in FIGS. 3a and 4. Immunoblotting with PA28β-specific polyclonal antibodies confirmed that PA28β is not expressed in PA28β−/− mice (FIG. 3c). Surprisingly, no PA28α was detected under native (FIG. 3b) or denatured conditions (FIG. 3c) in PA28β−/− mice. Pulse-chase experiments with $^{35}$S-labeled splenocytes showed that even under conditions of interferon induction less than 1% of the wild-type level of PA28α was detected in PA28β−/− mice. In addition, in PA28β−/− mice PA28α was rapidly degraded with a half-life of 2.5 hr (versus ~40 hr in wild-type littermates). Thus, PA28 functions in vivo as a hetero-oligomer, ruling out an in vivo role for PA28α as a homo-heptamer. These findings led us to conclude that PA28β−/− mice have a functional phenotype equivalent to mice defective in both PA28α and βloci.

Interestingly, compared to splenocytes from wild-type littermates, the number of interferon-inducible catalytic subunits LMP2/7 and MECL1 incorporated into the proteasomes was reduced, while their exchangeable, constitutively expressed subunits X, Y, and Z remained present in the proteasomes of the PA28β−/− splenocytes (arrows; FIG. 3a).

Figure 4:
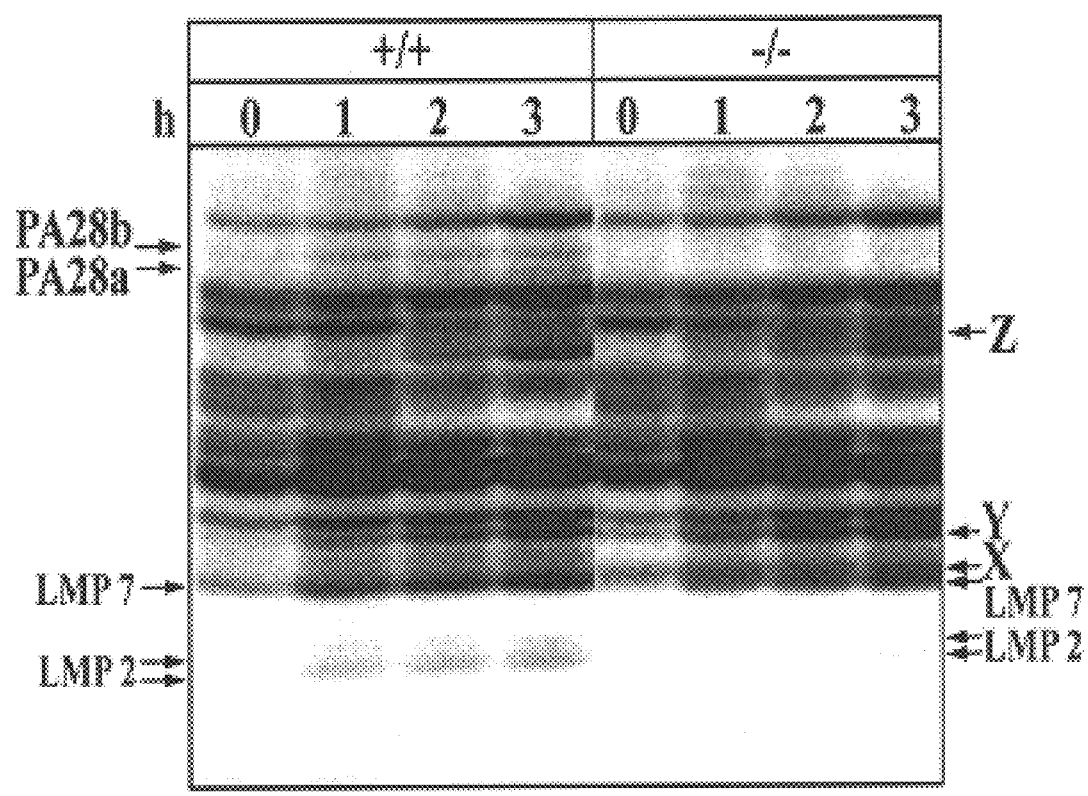
FIG. 4. Effect of PA28 on incorporation of proteasomal catalytic subunits. 24 hours after interferon induction the PA28β–/– and wildtype cells were metabolically labeled for 30 min and chased for the indicated times. Immunoprecipitations were performed with a C9-specific antiserum. Catalytic subunits, which were identified by 2-D gel electrophoresis and immunoblotting (Früh et al., 1994; Yang et al., 1995) with catalytic subunit-specific antisera, are indicated with arrows. The protein gel image is derived from a single representative fluorogram.

This finding, together with the observation that transient over-expression of PA28α, β, or both, results in an increase of immunoproteasome complexes without affecting the total cellular level of proteasomes, led us to hypothesize that PA28 might function as a chaperone to assist LMP2/7 and MECL1incorporation into the proteasome. To monitor the displacement of proteasomal catalytic subunits during the assembly of immunoproteasome we performed pulse-chase experiments. As shown in FIG. 4, analysis of proteasome assembly kinetics revealed that, after a 3-h chase, displacement of catalytic subunits X, Y, and Z by interferon-inducible subunits LMP2/7 and MECL1 is incomplete such that over 60% of X, Y and Z subunits remained present in the proteasomes of PA28β−/− cells, whereas X, Y, and Z subunits were completely displaced by LMP2/7 and MECL in wild-type cells. Moreover, even after an additional 24-h chase, over 25% of the X, Y, and Z subunits still remained present. Together with the findings that the expression levels of LMP2/7 and MECL1 were similar in both wild-type and PA28β−/− cells and that unincorporated LMP2/7 and MECL1 were rapidly degraded (Yang et al., 1995), these data strongly suggest that PA28 is required for the incorporation of interferon inducible catalytic subunits into the proteasome. We hypothesize that as a result of an increased cellular level of PA28-induced immunoproteasomes, which are responsible for the processing of hydrophobic peptides (FIG. 2a), production of peptides suitable for TAP translocation and presentation by class I molecules increases. Because PA28 appears to bind the immunoproteasome more tightly than the house-keeping proteasome and because immunoproteasomes are enriched on the endoplasmic reticulum membrane (Palmer et al., 1996; Rivett, 1998), it is conceivable that PA28 not only promotes immunoproteasome assembly but might also recruit immunoproteasomes to the endoplasmic reticulum membrane where TAP transporters are localized. Additionally, because PA28 binds to one or both ends of the cylindrical proteasome (Coux et al., 1996; Gray et al., 1994; Handil et al., 1998; Rock and Goldberg, 1999), PA28 might also control the binding and/or access of polypeptide substrates to the catalytic sites of the proteasome via its induction of an immunoproteasome conformational change (Conconi et al., 1999).

REFERENCES

Ahn, J. Y., Tanahashi, N., Akiyama, K.-Y., Hisamatsu, H., Noda, C., Tanaka, K., Chung, C. H., Shibmara, N., Willy, P. J., Mott, J. D., Slaughter, C. A., and DeMartino, G. N. (1995). Primary structures of two homologous subunits of PA28, a gamma-interferon-inducible protein activator of the 20S proteasome. FEBS Letters 366, 37–42.

Ahn, K., Erlander, M., Leturcq, D., Peterson, P. A., Frueh, K., and Yang, Y. (1996). In vivo characterization of the proteasome regulator PA28. J. Biol. Chem. 271, 18237–18242.

Bluthmann, H., Kisielow, P., Uematsu, Y., Malissen, M., Krimpenfort, P., Bems, A., von Boehmer, H., and Steinmetz, M. (1988). T-cell-specific deletion of T-cell receptor transgenes allows functional rearrangement of endogenous alpha- and beta-genes. Nature 334, 156–9.

Chu-Ping, M., Slaughter, C. A., and DeMartino, G. N. (1992). Identification, Purification, and Characterization of a protein activator (PA28) of the 20 S proteasome (Macropain). J. Biol. Chem. 267, 10515–10523.

Chu-Ping, M., Willy, P. J., Slaughter, C. A., and DeMartino, G. A. (1993). PA28, an activator of the 20 S proteasome, is inactivated by proteolytic modification at its carboxyl terminus. J. Biol. Chem. 268, 22514–22519.

Conconi, M., Djavadi-Ohaniance, L., Uerkvitz, W., Hendil, K. B., and Friguet, B. (1999). Conformational Changes in the 20S Proteasome upon Macromolecular Ligand Binding Analyzed with Monoclonal Antibodies. Arch. Biochem. Biophys. 362, 325–328.

Coux, O., Tanaka, K., and Goldberg, A. L. (1996). Structure and functions of the 20S and 26S proteasomes. Annu. Rev. Biochem. 65, 801–847.

Dick, T. P., Ruppert, T., Groettrup, M., Kloetzel, P. M., Kuehn, L., Koszinowski, U. H., Stevanovic, S., Schild, H., and Rammensee, H.-G. (1996). Coordinated dual cleavages induced by the proteasome regulator PA28 lead to dominant MHC ligands. Cell (Cambridge, Mass.) 86, 253–262.

Driscoll, J., Brown, M., Finley, D., and Monaco, J. (1993). MHC-linked LMP gene products specifically alter peptidase activities of proteasome. Nature 365, 262–264.

Dubiel, W., Pratt, G., Ferrell, K., and Rechsteiner, M. (1992). Purification of an 11 S regulator of the multicatalytic protease. J. Biol. Chem. 267, 22369–22377.

Fehling, H. J., Swat, W., Laplace, C., Kühn, R., Rajewsky, K., Müller, U., and Von Boehmer, H. (1994). MHC class I expression in mice lacking the proteasome subunit LMP-7. Science 265, 1234–1237.

Flad, T., Spengler, B., Kalbacher, H., Brossart, P., Baier, D., Kaufinann, R., Bold, P., Metzger, S., Bluggel, M., Meyer, H. E., Kurz, B., and Muller, C. A. (1998). Direct identification of major histocompatibility complex class I-bound tumor-associated peptide antigens of a renal carcinoma cell line by a novel mass spectrometric method. Cancer Res. 58, 5803–5811.

Fourie, A. M., and Yang, Y. (1998). Molecular requirements for assembly and intracellular transport of class I major histocompatibility complex molecules. Curr. Top. Microbiol. Immunol. 232, 49–74.

Früh, K., Gossen, M., Wang, K., Bujard, H., Peterson, P. A., and Yang, Y. (1994). Displacement of housekeeping proteasome subunits by MHC-encoded LMPs: s newly discovered mechanism for modulating the multicatalytic proteinase complex. EMBO J. 13, 3236–3244.

Fruh, K., Karlsson, L., and Yang, Y. (1997). Gamma interferon in antigen processing and presentation. Gamma Interferon Antiviral Def., 39–59.

Fruh, K., and Yang, Y. (1999). Antigen presentation by MHC class I and its regulation by interferon γ. Current Opinion in Immunology 11, 76–81.

Gaczynska, M., Goldberg, A. L., Tanaka, K., B, H. K., and Rock, K. L. (1996). Proteasome subunits X and Y alter peptidase activities in opposite ways to the interferon-γ-induced subunits LMP2 and LMP7. J. Biol. Chem. 271, 17275–17280.

Gaczynska, M., Rock, K., and Goldberg, A. (1993). Gamma-interferon and expression of MHC genes regulate peptide hydrolysis by proteasomes. Nature 365, 264–267.

Gaczynska, M., Rock, K. L., Spies, T., and Goldberg, A. L. (1994). Peptidase activities of proteasomes are differentially regulated by the major histocompatibility complex-encoded genes for LMP2 and LMP7. Proc. Natl. Acad. Sci. USA 91, 9213–9217.

Gray, C. W., Slaughter, C. A., and DeMartino, G. N. (1994). PA28 activator protein forms regulatory caps on proteasome stacked rings. J. Mol. Biol. 236, 7–15.

Groettrup, M., Soza, A., Eggers, M., Kuehn, L., Dick, T. P., Schild, H., Rammensee, H.-G., Koszinowski, U. H., and Kloetzel, P.-M. (1996). A role for the proteasome regulator PA28.alpha. in antigen presentation. Nature (London) 381, 166–168.

Handil, K. B., Khan, S., and Tanaka, K. (1998). Simultaneous binding of PA28 and PA700 activators to 20 S proteasomes. Biochem. J. 332, 749–754.

Jackson, M. R., Song, E. S., Yang, Y. A., and Peterson, P. A. (1992). Empty and peptide-containing conformers of class I major histocompatibility complex molecules expressed in Drosophila melanogaster cells. Proc. Natl. Acad. Sci. U. S. A. 89, 12117–21.

Jacoby, W., Cammarata, P. V., Findlay, S., and Pincus, S. H. (1984). Anaphylaxis in mast cell-deficient mice. J Invest Dermatol 83, 302–4.

Jameson, S. C., Carbone, F. R., and Bevan, M. J. (1993). Clone-specific T cell receptor antagonists of major histocompatibility complex class I-restricted cytotoxic T cells. J Exp Med 177, 1541–50.

Johnston, S. C., Whitby, F. G., Realini, C., Rechsteiner, M., and Hill, C. P. (1997). The proteasome 11 S regulator subunit REG.alpha. (PA28.alpha.) is a heptamer. Protein Sci. 6, 2469–2473.

Knowlton, J. R., Johnston, S. C., Whitby, F. G., Realini, C., Zhang, Z., Rechsteiner, M., and Hill, C. P. (1997). Structure of the proteasome activator REG.alpha. (PA28.alpha.). Nature (London) 390, 639–643.

Li, Y., Chambers, J., Pang, J., Ngo, K., Peterson, P. A., Leung, W.-P., and Yang, Y. (1998). Characterization of the mouse proteasome regulator PA28 b gene. Immunogenetics 49, 149–157.

Moore, M. W., Carbone, F. R., and Bevan, M. J. (1988). Introduction of soluble protein into the class I pathway of antigen processing and presentation. Cell 54, 777–85.

Palmer, A., Rivett, A. J., Thomson, S., Hendil, K. B., Butcher, G. W., Fuertes, G., and Knecht, E. (1996). Subpopulations of proteasomes in rat liver nuclei, microsomes and cytosol. Biochem. J. 316, 401–407.

Porgador, A., Yewdell, J. W., Deng, Y., Bennink, J. R., and Germain, R. N. (1997). Localization, quantitation, and in situ detection of specific peptide-MHC class I complexes using a monoclonal antibody. Immunity 6, 715–726.

Realini, C., Jensen, C. C., Zhang, Z.-g., Johnston, S. C., Knowlton, J. R., Hill, C. P., and Rechsteiner, M. (1997). Characterization of recombinant REG.alpha., REG.beta., and REG.gamma. proteasome activators. J. Biol. Chem. 272, 25483–25492.

Realini, C., Rogers, S. W., and Rechsteiner, M. (1994). Proposed roles in protein-protein association and presentation of peptides by MHC class I receptors. FEBS Lett. 348, 109–113.

Rivett, A. J. (1998). Intracellular distribution of proteasomes. Curr. Opin. Immunol. 10, 110–114.

Rock, K. L., and Goldberg, A. L. (1999). Degradation of cell proteins and the generation of MHC class I-presented peptides. Annu. Rev. Immunol. 1 7, 739–779.

Rock, K. L., Gramm, C., Rothstein, L., Clark, K., Stein, R., Dick, L., Hwang, D., and Goldberg, A. L. (1994). Inhibitors of the proteasome block the degradation of most cell proteins and the generation of peptides presented on MHC class I molecules. Cell 78, 761–771.

Song, X., Von Kampen, J., Slaughter, C. A., and Demartino, G. N. (1997). Relative functions of the alpha. and beta. subunits of the proteasome activator, PA28. J. Biol. Chem. 272, 27994–28000.

Van Kaer, L., Ashton-Rickard, P. G., Eichelberger, M., Gaczynska, M., Nagashima, K., Rock, K. L., Goldberg, A. L., Doherty, P. C., and Tonegawa, S. (1994). Altered peptidase and viral-specific T cell response in LMP2 mutant mice. Immunity 1, 533–541.

Vinitsky, A., Anton, L. C., Snyder, H. L., Orlowski, M., Bennink, J. R., and Yewdell, J. W. (1997). The generation of MHC class I-associated peptides is only partially inhibited by proteasome inhibitors: Involvement of non-proteasomal cytosolic proteases in antigen processing? J. Immunol. 159, 554–564.

Vitiello, A., Sette, A., Yuan, L., Farness, P., Southwood, S., Sidney, J., Chesnut, R. W., Grey, H. M., and Livingston, B. (1997). Comparison of cytotoxic T lymphocyte responses induced by peptide or DNA immunization: implications on immunogenicity and immunodominance. Eur J Immunol 27, 671–8.

Yang, Y., Frueh, K., Ahn, K., and Peterson, P. A. (1995). In vivo assembly of the proteasomal complexes, implications for antigen processing. J. Biol. Chem. 270, 27687–94.

Yang, Y., Sempe, P., and Peterson, P. A. (1996). Molecular mechanisms of class I major histocompatibility complex antigen processing and presentation. Immunol. Res. 15, 208–233.

What is claimed is:

1. A transgenic mouse whose somatic and germ cells comprise a homozygous disruption in the endogenous PA28β gene, wherein said disruption is generated by targeted replacement with a non-functional PA28β gene, and wherein said disruption results in impaired priming of cytotoxic T lymphocytes as compared to priming of cytotoxic T lymphocytes in wild-type PA28β mice.

2. The mouse of claim 1, wherein said mouse is fertile and capable of transmitting the disrupted PA28β gene to its offspring.

3. The mouse of claim 1, wherein the disrupted PA28β gene has been introduced into an ancestor of the mouse at an embryonic stage by microinjection of altered embryonic stem cells into mouse blastocysts.

4. The mouse of claim 1, wherein the altered PA28β gene has been introduced into the mouse at an embryonic stage either by microinjection or electroporation of altered embryonic stem cells into mouse blastocysts.

5. A cell line derived from the transgenic mouse of claim 1, wherein the cells of said cell line comprise a homozygous disruption in the endogenous PA28β gene.

6. A method of producing a transgenic mouse whose somatic and germ cells comprise a homozygous disruption in the endogenous PA28β gene, wherein said disruption is generated by targeted replacement with a non-functional PA28β gene, said method comprising:

(a) introducing a PA28β targeting construct comprising a selectable marker sequence into a mouse embryonic stem cell;

(b) introducing said embryonic stem cell into a mouse blastocyst;

(c) transplanting said blastocyst into a recipient mouse; and (d) allowing said blastocyst to develop to term;

(e) identifying a transgenic mouse whose genome comprises a disruption in the endogenous PA28β gene in at least one allele; and (f) breeding the transgenic mouse of step (e) to obtain a transgenic mouse whose genome comprises a homozygous disruption in the endogenous PA28β gene, wherein said disruption results in impaired priming of cytotoxic T lymphocytes as compared to priming of cytotoxic T lymphocytes in wild-type PA28β mice.

7. The method of claim 6 wherein the introducing of step (a) is by electroporation, and of step (b) is by microinjection.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Neomycin
      specific oligonucleotide

<400> SEQUENCE: 1
caaaaccaca ctgctcgaca ttg                                          23

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: PA28
      intron 2 specific oligonucleotide

<400> SEQUENCE: 2
gagtaaccca ccagttcacc ttaa                                         24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: PA28beta
      specific oligonucleotide probe

<400> SEQUENCE: 3
tccgaacctt catgcttact caag                                         24
```